United States Patent
Cabilly et al.

(10) Patent No.: US 6,379,516 B1
(45) Date of Patent: *Apr. 30, 2002

(54) APPARATUS AND METHOD FOR ELECTROPHORESIS

(75) Inventors: Shmuel Cabilly, Gedera; Uri Yogev, Yavne; Ilana Margalit, Ramat Gan, all of (IL)

(73) Assignee: Ethrog Biotechnology Ltd., Ness Zions (IL)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/734,929

(22) Filed: Oct. 22, 1996

Related U.S. Application Data

(63) Continuation-in-part of application No. 08/639,869, filed on Apr. 26, 1996, now Pat. No. 5,865,974, which is a continuation-in-part of application No. 08/427,917, filed on Apr. 26, 1995, now Pat. No. 5,582,702.

(51) Int. Cl.⁷ ........................ G01N 27/26; G01N 27/447
(52) U.S. Cl. ........................ 204/456; 204/450; 204/466; 204/600; 204/606; 204/616
(58) Field of Search ................................ 204/600, 606, 204/612, 616, 621

(56) References Cited

U.S. PATENT DOCUMENTS

| | | | | |
|---|---|---|---|---|
| 3,715,295 A | * | 2/1973 | Tocci | 204/606 |
| 3,764,513 A | * | 10/1973 | Saravis | 204/616 |
| 4,323,439 A | | 4/1982 | O'Farrell | 204/180 |
| 4,874,491 A | | 10/1989 | Stalberg | 204/182.8 |
| 4,892,639 A | | 1/1990 | Sarrine et al. | 204/229 |
| 5,006,473 A | * | 4/1991 | Bouma et al. | 436/516 |
| 5,045,164 A | | 9/1991 | Tansamrit et al. | 204/182.8 |
| 5,106,477 A | | 4/1992 | Coleman et al. | 204/299 |
| 5,209,831 A | | 5/1993 | MacConnell | 204/299 |
| 5,407,552 A | | 4/1995 | Lebacq | 204/299 |
| 5,411,657 A | | 5/1995 | Leka | 204/299 |
| 5,582,702 A | | 12/1996 | Cabilly et al. | 204/456 |

FOREIGN PATENT DOCUMENTS

WO     WO 87/04948     2/1987

OTHER PUBLICATIONS

Anthony T. Andrews "Electrophoresis: Theory, Techniques, and Bio–Chemical and Clinical Applications, 2nd edition" p. 79, 1986.*

* cited by examiner

*Primary Examiner*—Jill Warden
*Assistant Examiner*—John S. Starsiak, Jr.
(74) *Attorney, Agent, or Firm*—Eitan, Pearl, Latzer & Cohen-Zedek

(57) ABSTRACT

Apparatus for conducting electrophoresis separation therein. The apparatus includes a chamber having therein a body of separating gel for carrying therein an electrophoresis separation and electrodes for connecting the chamber to an external electrical power source, thereby driving the electrophoresis separation. According to the invention at least one of the electrodes also providing ions for driving the electrophoresis separation. In one preferred embodiment, the apparatus is a cassette substantially closed before, during and after electrophoresis separation. According to an aspect of the invention the pH in the body of separating gel is substantially constant during the electrophoresis separation.

35 Claims, 11 Drawing Sheets

APPARATUS AND METHOD FOR ELECTROPHORESIS

CROSS REFERENCE TO OTHER APPLICATIONS

This application is a continuation in part application of U.S. Ser. No. 08/639,869 filed Apr. 26, 1996 now U.S. Pat. No. 5,865,974 which is a continuation in part application of U.S. Ser. No. 08/427,917 filed Apr. 26, 1995 now U.S. Pat. No. 5,582,702.

FIELD OF THE INVENTION

The present invention relates to electrophoresis generally and more particularly to apparatus for conducting an electrophoresis test therein.

BACKGROUND OF THE INVENTION

A great deal of diagnostic procedures and laboratory research are carried out wherein DNA, RNA or proteins are separated according to their physical and chemical properties via electrophoresis. This process is widely used and has many applications. For example, it is used to analyze DNA molecules according to their resultant size after being digested by restriction enzymes. It is also used to analyze the products of a polymerase chain reaction (PCR).

Typically, electrophoresis separation is carried out in a separation medium, such as a gel of agarose or acylamide or a combination of the two. Usually, agarose gels are cast in open trays and form a slab whereas acrylamide gels are cast between two glass plates.

In order to effect the electrophoretic separation, two opposite ends of the gels are exposed to an electrically conducting buffer which is connected by electrodes, typically carbon or platinum, to an electric power source. Once the electrical power source is switched on, the electric field forces negatively charged molecules to move towards the anode and positively charged molecule to move towards the cathode. One characteristic of conventional electrophoresis is the use of large volumes of buffer having a relatively low salt concentration to maintain the required electric field.

DNA is negatively charged and therefore, in the agarose or acrylamide gels which provide sieving action, DNA molecules move towards the anode at a rate which depends on their size, wherein the smaller the molecules the faster they move.

In the electrophoretic separation of proteins, the proteins are often treated with an ionic detergent, such as sodium dodecylsulphate (SDS). The negatively charged dodecylsulphate anions interact with hydrophobic domains on the protein molecules, thus creating negatively charged protein/SDS complexes that undergoing electrophoresis separation similarly to DNA molecules.

Typically, it is desirable to visualize and to document the results of the electrophoretic separation test. In electrophoretic separation of DNA molecules, this has been done by immersing the gel slab after the electrophoretic separation has been completed in a solution of a fluorescent compound which emits visible light when exposed to a ultra violet (UV) light. A widely used compound in ethidium bromide.

Conventional electrophoretic separation systems are deficient in many respects, a few of which are listed below.

Prior art electrophoresis separation systems are a potential source of contamination to the working environment in which the tests are performed. The two major sources of contamination are ethidium bromide and PCR products. Ethidium bromide is a hazardous chemical due to its mutagenic activity and therefore, exposure to ethidium bromide may induce malignant tumors. PCR is an extremely sensitive method to the extent that a single molecule of DNA product from one PCR (out of the trillions of molecules being produced) may interfere with the subsequent PCR such that it will produce incorrect result.

Conventional electrophoresis is also deficient in other respects, one being that it is time consuming.

Various attempts have been made to solve the deficiencies of conventional electrophoresis. Most attempts have been addressed to overcome the deficiency of conventional electrophoresis systems with respect to the use of buffers therein.

U.S. Pat. No. 4,874,491 to Stalberg describes an electrophoresis system having a high concentration buffer containing gel.

U.S. Pat. No. 4,892,639 to Sarrine et al. describes an electrophoresis plate with improved buffer circulation.

U.S. Pat. No. 5,045,164 to Tansamrit et al. describes an electrophoresis plate having thickened ends as buffer reservoirs.

U.S. Pat. No. 5,209,831 to MacConnel describes a bufferless disposable cassette having open ends and conductive film electrodes.

U.S. Pat. Nos. 5,407,552 to Lebacq and 5,411,657 to Leka describe open electrophoresis devices requiring a buffer tank for operation.

SUMMARY OF THE INVENTION

It is therefore an object of the present invention to provide an improved apparatus for electrophoresis.

A major object of the present invention is to provide a closed cassette for electrophoresis which is substantially closed before, during and after an electrophoresis test conducted therein.

According to an aspect of the present invention the cassette is a disposable cassette.

The cassette of the present invention overcomes drawbacks associated with prior art electrophoresis cassettes, plates or slabs. Since the cassette is a closed one, its outer environment is not susceptible to contamination. Moreover, since it is ready to use, the preparation time required for preparing prior art cassettes is saved.

Another object of the present invention is to provide an electrophoresis system in which both the electrophoretic separation and the visualization of the results thereof are done while the cassette is in situ.

According to one aspect of the present invention, there is provided a substantially closed disposable cassette with openings for introducing a sample of molecules thereinto, the openings being preferably opened only just before the electrophoresis test.

According to another aspect of the present invention, the cassette includes all the chemical compounds required to drive the electrophoretic separation.

In accordance with yet another aspect of the present invention, when DNA, RNA and protein molecules are separated, the cassette includes the compounds required to stain the separated DNA, RNA and proteins, respectively.

According to yet another aspect of the invention, the volume of the ion source utilized for providing the ions required for the electrophoresis separation is smaller than the volume of the gel utilized as the electrophoresis separation matrix and preferably smaller than the volume of gel utilized for actual separation during an electrophoresis test.

According to a preferred embodiment of the present invention, the ions (cations and anions) required to drive the electrophoretic separation are provided by a cation exchange matrix and an anion exchange matrix, respectively.

According to another preferred embodiment of the present invention, the ions exchange matrix also provides the ions required to stain the separated molecules in order to enable visualization thereof when the cassette is illuminated with a UV light source in the case of DNA molecules separation and with a visible light source when protein molecules are being electorphoretically separated.

According to an alternative embodiment of the present invention the ions required to drive the electrophoresis separation are provided by a reservoir, preferably a breakable ampoule containing a buffer characterized by relatively high concentration of these ions.

One advantage of the cassette of the present invention is that it is disposable.

Another advantage of the cassette of the present invention is that the user is not exposed to any hazardous chemical constituent, such as ethidium bromide, as in prior art cassettes.

Yet another advantage of the cassette of the present invention is that PCR-DNA products are contained within the cassette and are disposed therewith so as to substantially reduce the contamination of the working environment in which the tests are performed.

There is thus provided, in accordance with a preferred embodiment of the present invention, an apparatus for conducting electrophoresis separation therein which includes a housing having at least bottom and side walls defining a chamber, wherein the chamber includes in contact therebetween a body of gel for carrying therein the electrophoresis separation, at least one ion source for providing ions for driving the electrophoresis, the at least one ion source having a volume smaller than the volume of the body of gel, and electrodes for connecting the chamber to an external electrical power source, thereby enabling to drive the electrophoresis separation.

There is also provided, in accordance with a preferred embodiment of the present invention a substantially closed cassette for conducting therein electrophoresis separation, the cassette being closed before, during and after electrophoresis separation, which includes a closed chamber which includes therein a body of gel for carrying therein the electrophoresis separation, at least one ion source for providing ions for driving the electrophoresis separation, and electrodes for connecting the cassette to an external electrical power source, thereby enabling to drive the electrophoresis separation.

According to a preferred embodiment, the volume of the at least one ion source is smaller than the volume of the body of gel utilized in the electrophoresis separation.

In a preferred embodiment, the at least one ion source includes a body of ion exchange matrix. Further, the body of ion exchange matrix includes a body of cation exchange matrix for providing the cations for driving the electrophoresis separation and a body of anion exchange matrix for providing the anions for driving the electrophoresis separation. Still further, the cation exchange matrix is disposed at one end of the body of separating gel and the body of anion exchange matrix is disposed on a second end of the separating gel.

In operation, the cation exchange matrix exchanges protons derived from electrolysis with the cations for driving the electrophoretic separation and the anion exchange matrix exchanges hydroxyl ions derived from the electrolysis with the anions for driving the electrophoretic separation.

According to a preferred embodiment of the present invention, the cation exchange matrix and the anion exchange matrix includes particles immersed in a support matrix. Preferably, the support matrix is formed of the gel as the body of gel for carrying the electrophoresis separation therein.

In accordance with yet a further embodiment of the present invention, the apparatus also include an additional body of gel of low gel strength disposed between the side wall of the chamber and the anion exchange matrix, the body of gel of low gel strength shrinking during the electrophoresis separation, thereby providing a volume in which gases produced at the vicinity of an anode of the chamber accumulates.

Further, according to a preferred embodiment of the present invention, the apparatus includes a buffer solution in contact with the body of separating gel, the at least one body of ion exchange matrix and the electrodes. Preferably, the buffer is a TAE buffer, thus the cation exchange matrix releases Tris cations and the anion exchange matrix releases acetate anions.

Additionally, according to a preferred embodiment of the present invention, the cation exchange matrix includes ethidium cations.

In accordance with an alternative embodiment of the present invention, the at least one ion source includes a closed reservoir having therein a buffer solution having higher concentrations than a concentration of a buffer solution of the body of gel for carrying therein the electrophoresis separation, the closed reservoir being opened just before the electrophoresis separation for providing the ions for driving the electrophoresis separation.

In a preferred embodiment, the closed reservoir is a breakable ampoule. Further, the breakable ampoule may be surrounded by a space, the space at least partially filled with the buffer solution in a concentration generally similar to that of the body of gel for carrying therein the electrophoresis separation. Preferably, the buffer is a TAE buffer. In addition, the buffer may also include ethidium cations.

The apparatus and cassette of the present invention are further characterized by any combination of the following features:

The chamber or the cover may include at least one opening therein for introducing at least one test sample into the body of gel. Preferably, the at least one opening is closed by a comb prior to the electrophoresis separation.

The chamber and/or the cover may be transparent to ultra violet (UV) radiation.

The chamber or cover may also include at least one vent hole which is closed prior to the electrophoresis test and is being opened just before the electrophoresis test.

Further, according to a preferred embodiment of the present invention, the electrodes include a conductive material capable of adsorbing at least part or at least one of the gases produced during the electrophoresis separation. Preferably, the at least one electrode capable of adsorbing is substantially formed from a material selected from the group consisting of aluminum and palladium.

Additionally, the gases include oxygen created at the vicinity of the anode during the electrophoresis separation and reacting with the aluminum. Alternatively, the gases include hydrogen created at the vicinity of the cathode during the electrophoresis separation and wherein the hydrogen is adsorbed by the palladium.

In an alternative embodiment, the at least one electrodes includes a strip of conductive material. Preferably, the strip of conductive material is mounted on a ramp, the ramp being inclined at an angle relative to the bottom wall, whereby gases produced at the vicinity of the strip during the electrophoresis separation are being directed to an empty volume receiving the gases.

Finally, the apparatus or cassette may also include at least one empty volume for accumulating gases produced during the electrophoresis test.

There is also provided, in accordance to a preferred embodiment of the present invention a system for conducting electrophoresis separation which includes an electrical power source, a substantially closed disposable cassette substantially closed before, during and after electrophoresis separation therein, preferably, but not necessarily, the apparatus or cassette of the present invention, and a support for supporting the substantially closed cassette and for connecting the electrical power source to the conductive elements of the cassette.

Further, the system may also include a UV light source and wherein the cassette is transparent to UV light, and wherein the cassette also includes a UV sensitive material capable of interacting with the molecules undergoing electrophoresis separation and of emitting light, thereby enabling to conduct the electrophoresis separation and to visualize it while the cassette is in situ. In a preferred embodiment, the UV sensitive material is ethidium bromide.

Still further, the system may also include camera means for documenting the results of the electrophoresis separation. The system may also include a computer which includes at least one image analysis application for analyzing the results of the electrophoresis separation.

Additionally, the system may include a cooling system for cooling the cassette during the electrophoresis test.

There is also provided, in accordance with a preferred embodiment of the present invention, an electrophoresis method which includes the steps of introducing at least one test sample into a body of gel, applying an electrical field to the body of gel and driving an electrophoresis separation by providing ions required for driving the electrophoresis separation by at least one ion source having a volume smaller than the volume of the gel.

Further, there is also provided, in accordance with a preferred embodiment of the present invention, a method for producing a substantially closed cassette for conducting electrophoresis separation therein which includes the steps of providing a housing having bottom and side walls defining an open chamber, assembling within the chamber in contact therebetween a body of gel for carrying therein the electrophoresis separation, at least one ion source for providing ions for driving the electrophoresis separation, the at least one ion source having a volume smaller than that of the body of gel and electrodes for connecting the chamber to an external electrical power source, and closing the open housing with a cover, thereby forming a substantially closed cassette capable of carrying the electrophoresis separation therein.

Still further, there is also provided, according to yet another preferred embodiment of the present invention apparatus for conducting electrophoresis separation therein which includes a chamber having therein a body of separating gel for carrying therein the electrophoresis separation and electrodes for connecting the chamber to an external electrical power source, thereby driving the electrophoresis separation, at least one of the electrodes also providing ions for driving the electrophoresis separation.

Further, according to a preferred embodiment, the electrophoretic separation is substantially free from water electrolysis and the pH is generally constant throughout the body of separating gel.

Still further, the chamber may also include a dye source for providing a dye, the dye enabling visualization of the electrophoresis separation.

In accordance with one preferred embodiment, the electrode providing the ions is the anode. Further, during the electrophoresis separation an electrochemical reaction wherein metal atoms of the anode loose electrons and enter solution as cations occurs preferentially to electrolysis of water molecules.

In a preferred embodiment, the anode is selected from the group consisting of lead, silver and copper.

According to yet another preferred embodiment, the anode is in contact with a body of a cation exchange matrix for binding the ions provided by the anode thereby releasing other ions for driving the electrophoresis separation.

In an alternative embodiment, the cathode is in contact with a salt suspended in a support matrix, the salt is insoluble in water. During electrophoresis separation an electrochemical reaction wherein cations of the salt receive electrons from the cathode occurs preferentially to electrolysis of water molecules.

In a preferred embodiment, the cathode is selected from the group consisting of lead and silver and copper and the salt is selected from the group consisting of lead carbonate and silver chloride.

In another preferred embodiment, the anode is in contact with a salt suspended in a support matrix and the cathode end is in contact with a body of cation exchange matrix.

In yet another preferred embodiment, the chamber includes a body of stacking gel, the body of stacking gel being in contact with the body of separating gel.

BRIEF DESCRIPTION OF THE DRAWINGS

The present invention will be understood and appreciated more fully from the following detailed description taken in conjunction with the appended drawings in which.

DETAILED DESCRIPTION OF THE PRESENT INVENTION

Figure 1:
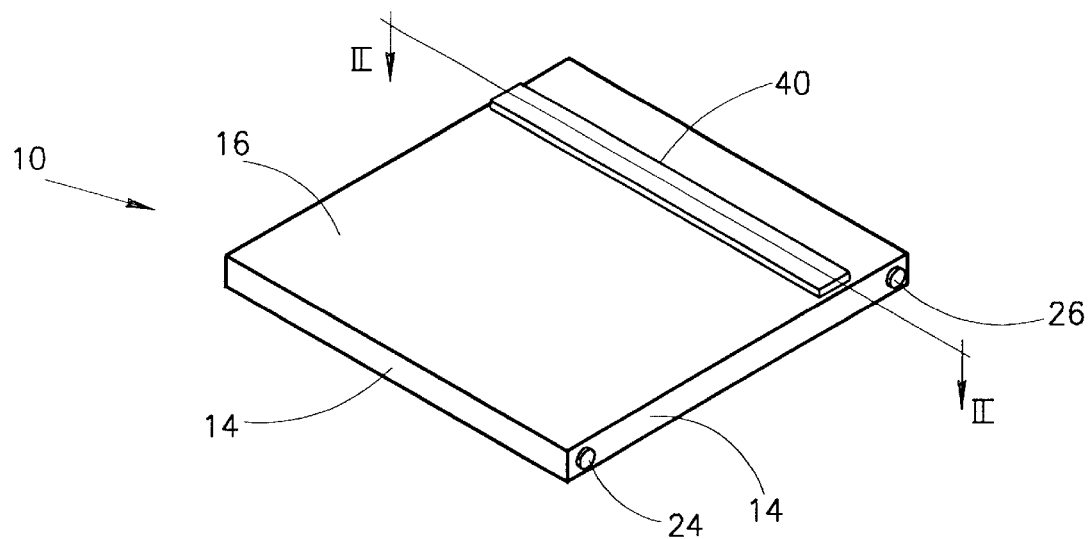
FIG. 1 is a schematic isometric illustration of an electrophoresis cassette, constructed and operative in accordance with a preferred embodiment of the present invention.

It is noted that for a better understanding, like components are designated by like reference numerals throughout the various figures.

Reference is now made to FIGS. 1–4 which illustrate an electrophoresis disposable cassette, generally referenced 10, constructed and operative in accordance with a preferred embodiment of the present invention.

Cassette 10, as best seen in FIG. 1, is a closed disposable cassette preferably, but not necessarily, used for a single electrophoresis test. Cassette 10 includes all the chemical compounds required for driving the electrophoresis separation and for enabling visualization of its results when DNA as well as RNA or protein molecules have been separated.

Figure 3:
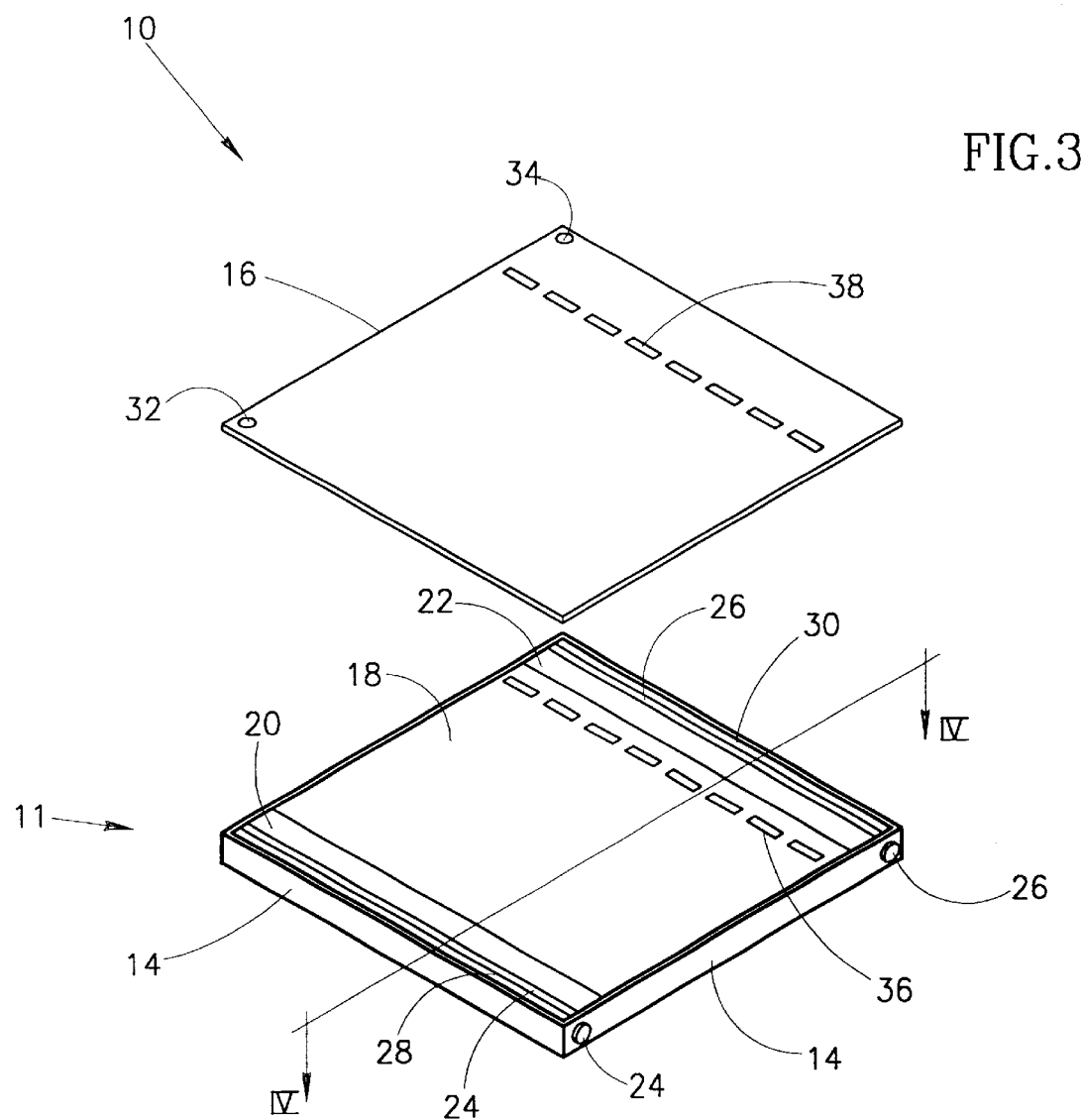
FIG. 3 is a schematic isometric exploded illustration of the electrophoresis cassette of FIG. 1.

As best seen in FIG. 3, the cassette 10 preferably comprises a three dimensional chamber 11 which is preferably substantially flat, having bottom wall and side walls, referenced 12 and 14 respectively, and a cover 16 which forms the top wall of the cassette. The bottom wall 12 (FIG. 4) and the cover 16 are preferably made of any suitable UV transparent material, such as the TPX plastic commercially available from MITSUI of Japan or the PMMA plastic, commercially available from Repsol Polivar S.P.A. of Rome. In a preferred method for producing cassette 10 a plastic molding process is employed utilizing a Rohaglas Molding Powder, commercially available from Sidas GmbH of Damstadt, Germany.

Figure 4:
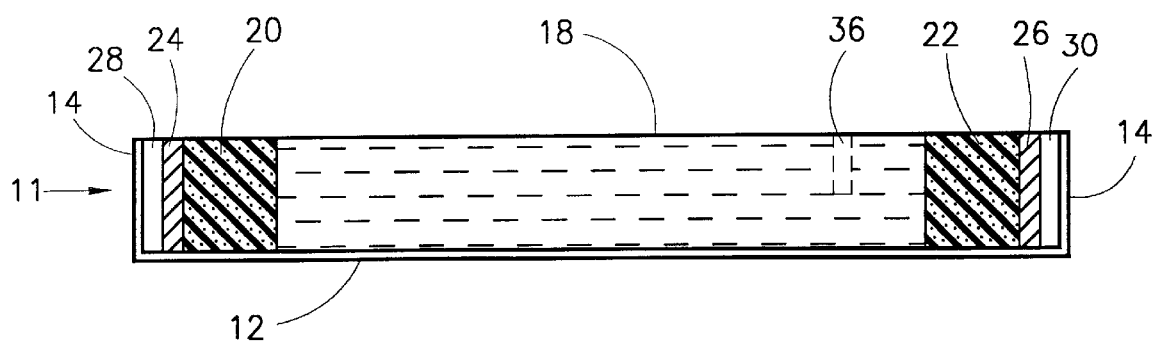
FIG. 4 is a schematic cross section illustration along lines IV—IV in FIG. 3.

As best seen in the cross section illustration of FIG. 4, chamber 11 preferably comprises a gel matrix 18 which may be any suitable gel matrix for electrophoresis, such as an aqueous gel or a gel made of acrylamide, a cation exchange matrix 20 and an anion exchange matrix 22, collectively referred to as the ion exchange matrices 20 and 22. Chamber 11 further comprises two conductive rods referenced 24 and 26, such as stainless steel rods which, when connected to an external direct current (DC) electrical power source, provide the electric field required to drive electrophoretic separation. In the illustrated embodiment, rod 24 is the anode and rod 26 is the cathode. Chamber 11 further comprises two empty volumes 28 and 30, in which gases produced during the electrophoresis test may accumulate. Alternatively, the open cover 16 may include two vent holes 32 and 34, shown only in FIG. 3, for venting the gases accumulated in the empty volumes 28 and 30.

A particular feature of cassette 10, as best shown in FIGS. 3 and 4 is that the volume of the ion source, the ion exchange matrices 20 and 22 in the illustrated embodiment, is smaller than the volume of the gel 18 utilized as the electrophoresis separation matrix and preferably smaller than the volume of gel utilized for actual separation during an electrophoresis test.

It will be appreciated that if cassette 10 includes vent holes 32 and 34 they are sealed prior to the beginning of the electrophoretic test, and are opened just before the electrophoresis test begins and are closed again after the test is completed to substantially reduce the possibility of contamination originated therefrom.

Preferably, each of the gel 18, the ion exchange matrices 20 and 22 and the conductive rods 24 and 26 are in contact and are immersed in a relatively small amount of an agarose matrix produced and including a buffer solution, such as a Tris Acetate EDTA buffer, which facilitates the mobility of the molecules undergoing separation and of the ions provided by the ion exchange matrices 20 and 22.

It is a particular feature of the present invention that the ions required for driving the electrophoretic separation are provided by the ion exchange matrices 20 and 22, preferably, by exchanging with protons and hydroxyl ions derived from electrolysis of $H_2O$. In operation, a DC current is applied via rods 24 and 26 to initiate the electrolysis which in turn initiates the operation of the ion exchange matrices.

The cation exchange matrix 20 and the anions exchange matrix 22 release the cations and anions required for driving electrophoresis separation. An example of a suitable cation is the $Tris^{(+)}$ cation and an example of a suitable anion is $acetate^{(-)}$. Preferably, but not necessarily, the ions released by the ion exchange matrices 20 and 22 are exchanged with adsorbed protons and hydroxyl anions, respectively. Alternatively, or in addition thereto, the ions adsorbed by the ion exchange matrices 20 and 22 may also be provided by the rods 24 and 26.

It will be appreciated that the use of the ion exchange matrices 20 and 22 provides a generally uniform pH throughout the cell since any proton buildup near the anode 24 is compensated by absorption thereof by the neighboring cation exchange matrix 20 and hydroxyl buildup near the cathode 26 is compensated by absorption thereof by the anion exchange matrix 22.

According to one preferred embodiment of the present invention, the cation exchange matrix 20 and the anion exchange matrix 22 may be immersed in one of the materials used for preparing the gel.

A suitable cation exchange material is the CM-25-120 Sephadex and suitable anion exchange materials are the WA-30 and the A-25-120, all of which are commercially available from Sigma Inc. of St. Louis, U.S.A.

Cassette 10 preferably also includes wells 36 in the gel 18. Wells 36 are used to introduce samples of the molecules which are to undergo electrophoretic separation. The wells 36 may be formed by any suitable method, such as by introducing a comb like structure 40 (FIG. 2) to the gel during the assembly of the gel. The comb 40 is introduced to the gel via corresponding openings 38 (FIG. 1) in the cover 16. The openings 38 may be used as an additional space for loading the molecular samples just before the onset of the electrophoresis test after the comb 40 is removed.

Figure 2:
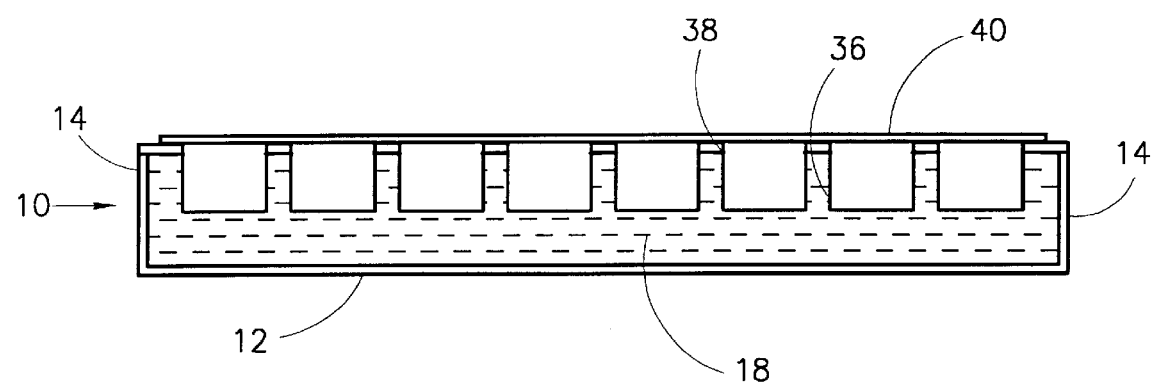
FIG. 2 is a schematic cross section illustration along lines II—II in FIG. 1.

According to a preferred embodiment of the present invention, as best seen from FIG. 2, the wells 36 are covered by the comb 40 used in their preparation. This is since the comb method involves insertion of a comb structure into the gel via the openings 38 in the top cover 16, the comb being pulled out only just before the electrophoresis test.

It is a particular feature of the present invention that the cassette 10 is a closed cassette covered by the comb 40 which is removed just before the electrophoresis test itself.

The cassette 10 also includes a source for ethidium cations which are used for ultra violet (UV) visualization of the separated DNA molecules. Unlike prior art electrophoresis systems, in which ethidium bromide is introduced after separation of the molecules, typically by immersing the gel in an ethidium bromide solution, the cassette 10 includes an internal source for ethidium ion source. Preferably, the cation exchange matrix 20 releases not only the TRIS cations but also ethidium cations which interact with the molecules undergoing electrophoretic separation.

In a preferred embodiment, the cation exchange matrix 20 provides a continuous flux of ethidium cations during the electrophoresis test so as to stain the DNA molecules so as to enable their visualization and analysis, in situ, utilizing a suitable electrophoresis system, such as the system described with reference to FIG. 16 hereinbelow.

The following examples, which are not intended to limit the scope of the present invention, illustrate how the cation exchange matrix 20 and the anion exchange matrix 22 are prepared. The following example is for a cassette whose outer length, width and height are 100 millimeters (mm), 80 mm, and 6 mm, respectively. It will be appreciated that a cassette of these outer dimensions is substantially flat.

EXAMPLE 1

The cation exchange matrix 20 was prepared as follows:
A. About 5 grams of CM-25-120 Sephadex particles were washed using three volume of TAE solution in a concentration 50 times higher than the concentration of the TAE buffer used during the electrophoresis test (herein X50 TAE solution). In this example, the concentration used in the electrophoresis test itself was 0.04 Molar of the acetate with 0.002 Molar EDTA.
B. The CM-25-120 Sephadex particles were washed by distilled water.
C. Two grams of the washed CM-25-120 Sephadex particles were mixed with 50 ml 0.5 X TAE buffer and 5 microliter of ethidium bromide.
D. The mixture was left without agitation for an hour so as to let the CM-25-120 particles to settle.
E. 25 ml of the mixture were filtered out so as to obtain a 25 ml solution including the 2 grams CM-25-120 Sephadex particles.
F. The obtained 25 ml mixture including the CM-25-120 Sephadex particles were immersed in a 4 percent agarose gel to obtain the cation exchange matrix 20.

The anion exchange matrix 22 is prepared as follows:
A. About 3 grams of WA-30 particles were washed using three volumes of the 50X solution used to wash the cation exchange particles.
B. The WA-30 particles were washed by distilled water.
C. One gram of the WA-30 particles was immersed in a 4 percent agarose gel to obtain the anion exchange matrix 22.

EXAMPLE 2

The cation exchange matrix 20 is prepared as follows:
A. 20 grams of swollen CM-25-120 Sephadex particles were placed in a standard column and washed with 500 ml of 1 Molar Tris base solution, having a pH of 9.3 as adjusted with HCl.
B. The CM-25-120 Sephadex particles were washed with 7 volumes of distilled water.
C. The CM-25-120 Sephadex particles were removed from the column and kept in two volumes of 0.6 X TAE buffer.
D. 1 ml of swollen CM-25-120 Sephadex were absorbed with ethidium bromide to saturation and the bromide ions were washed out.
E. 1.2 ml of the particles CM-25-120 kept in the TAE buffer (step C) and 3 microliter of the particles adsorbed with ethidium (step D) were immersed with 1.5 ml of 2% agarose gel which forms the agarose matrix to obtain the cation exchange matrix 20 for cassette 10.

The anion exchange matrix 22 was prepared as follows:
A. 25 grams of DEAE Sephadex A-25-120 particles were placed in a standard column and washed with 500 ml 1 Molar sodium acetate solution of pH 7 adjusted with acetic acid.
B. The A-25-120 particles were washed with 7 volumes of distilled water.
C. The A-25-120 Sephadex particles were removed from the column and kept in two volumes of 0.6 X TAE buffer.
D. 1.2 ml of the particles A-25-120 adsorbed with acetate ions (steps C) were immersed with 1.5 ml of 2% agarose gel which forms the agarose matrix to obtain the anion exchange matrix 22 for cassette 10.

Figure 5:
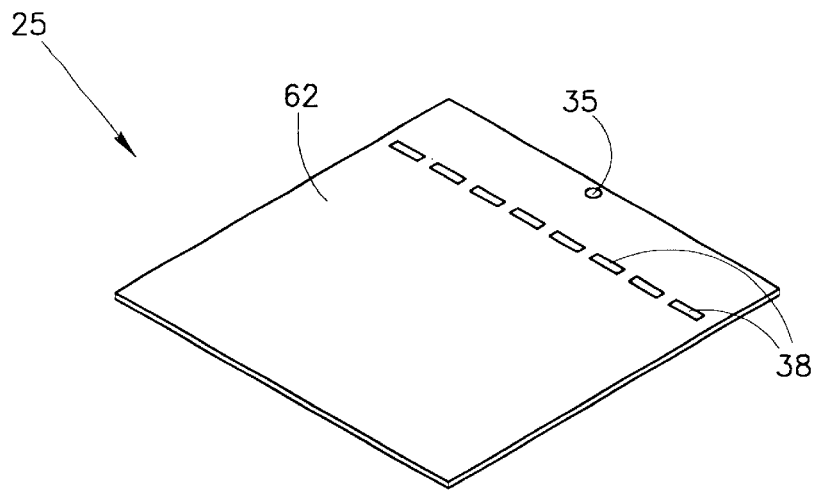
FIG. 5 is a schematic isometric exploded illustration of an electrophoresis cassette, constructed and operative in accordance with another preferred embodiment of the present invention.
Figure 6:
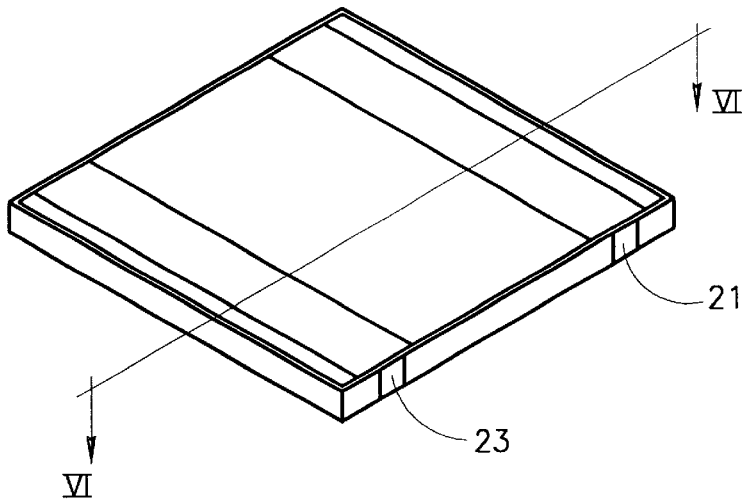
FIG. 6 is a schematic cross section illustration along lines VI—VI in FIG. 5.
Figure 6:
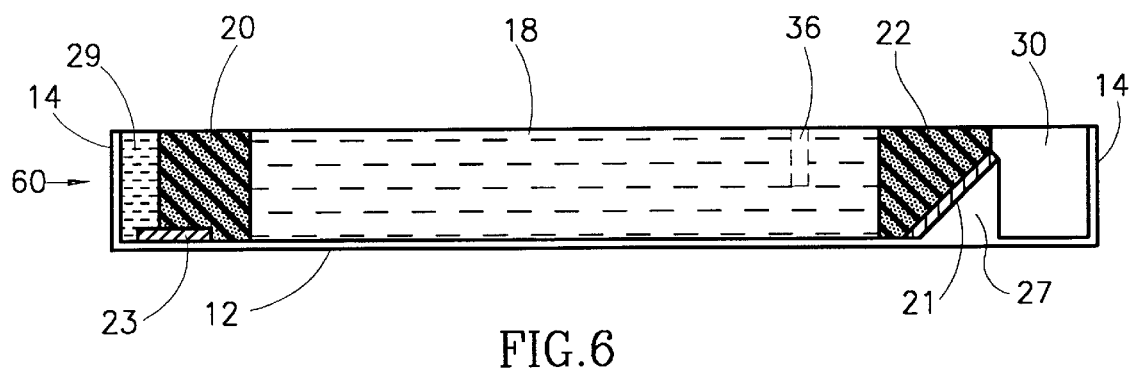
Figure 7:
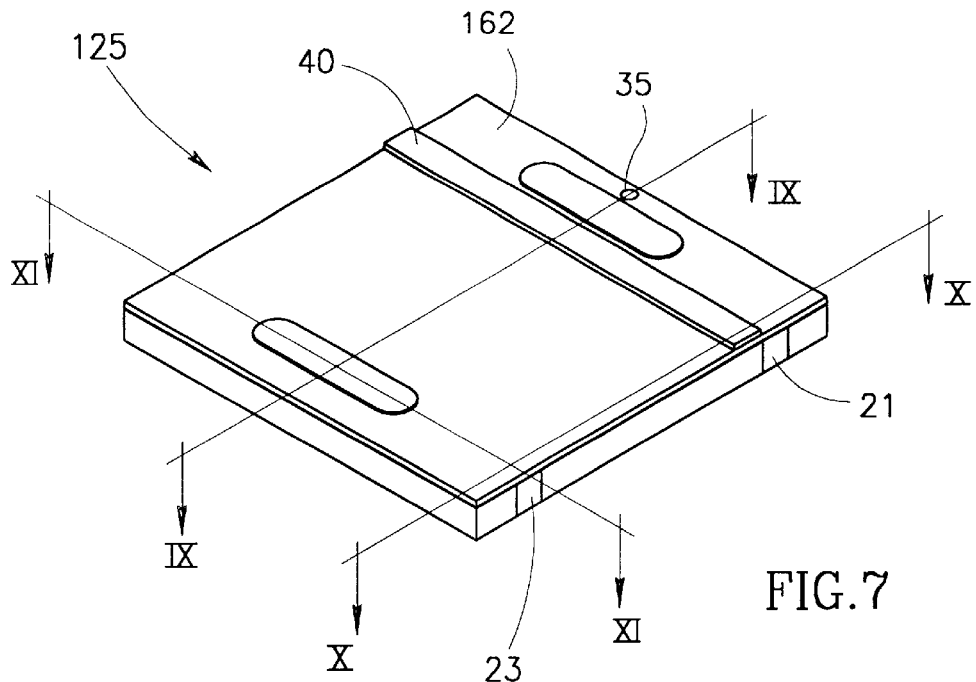
FIG. 7 is a schematic isometric illustration of an electrophoresis cassette, constructed and operative in accordance with a further preferred embodiment of the present invention.
Figure 8:
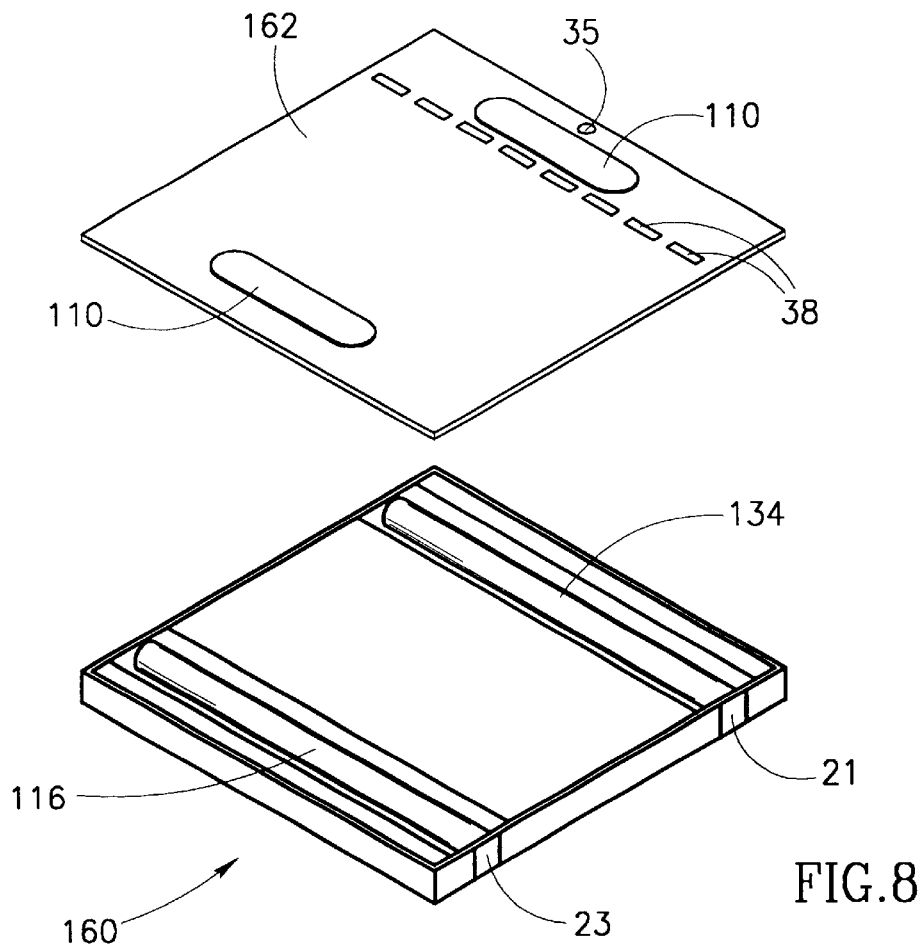
FIG. 8 is a schematic isometric exploded illustration of the electrophoresis cassette of FIG. 7.
Figure 9:
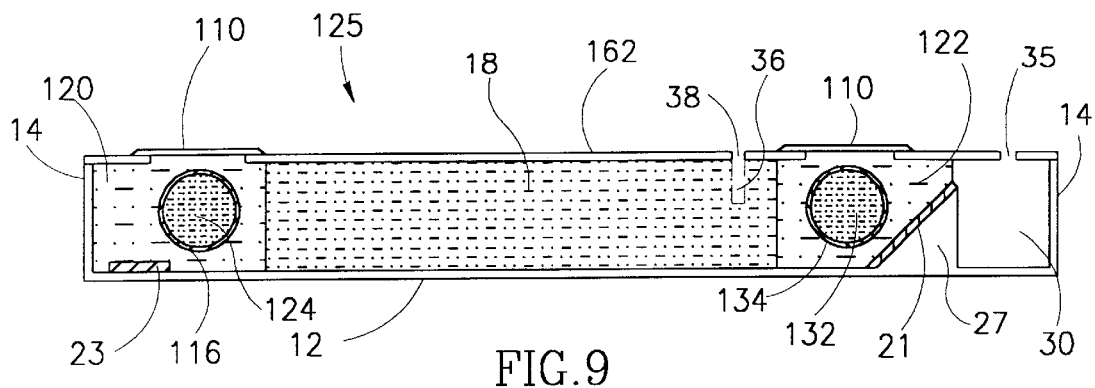
FIG. 9 is a schematic cross section illustration along lines IX—IX in FIG. 7.
Figure 10:
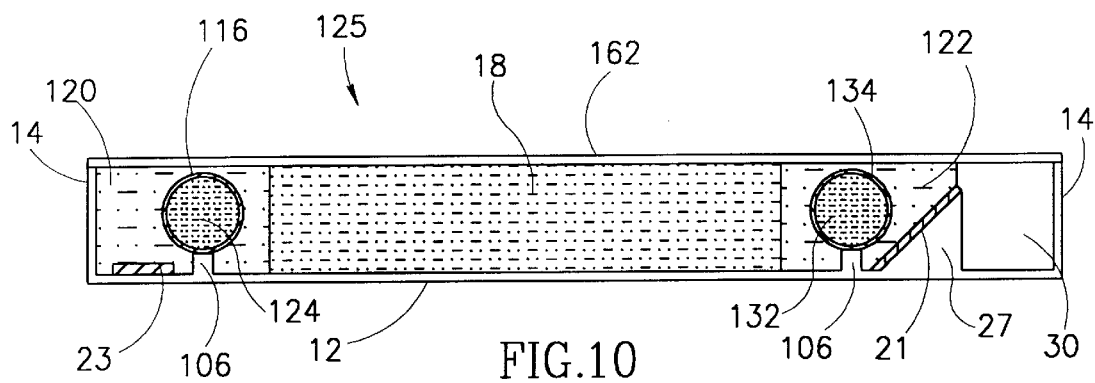
FIG. 10 is a schematic cross section illustration along lines X—X in FIG. 7.
Figure 11:
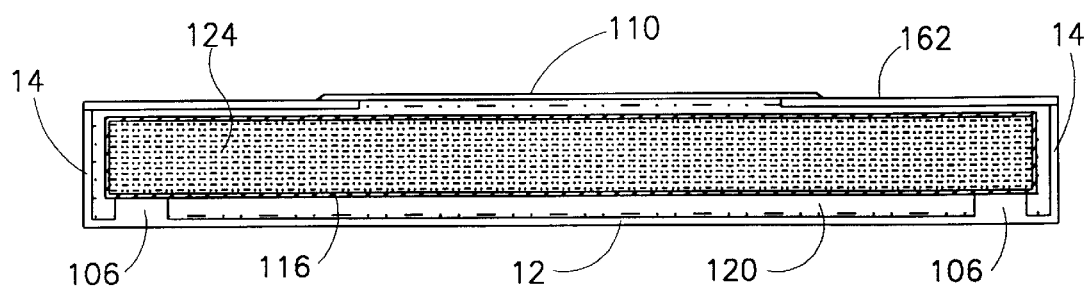
FIG. 11 is a schematic cross section illustration along lines XI—XI in FIG. 7.
Figure 12:
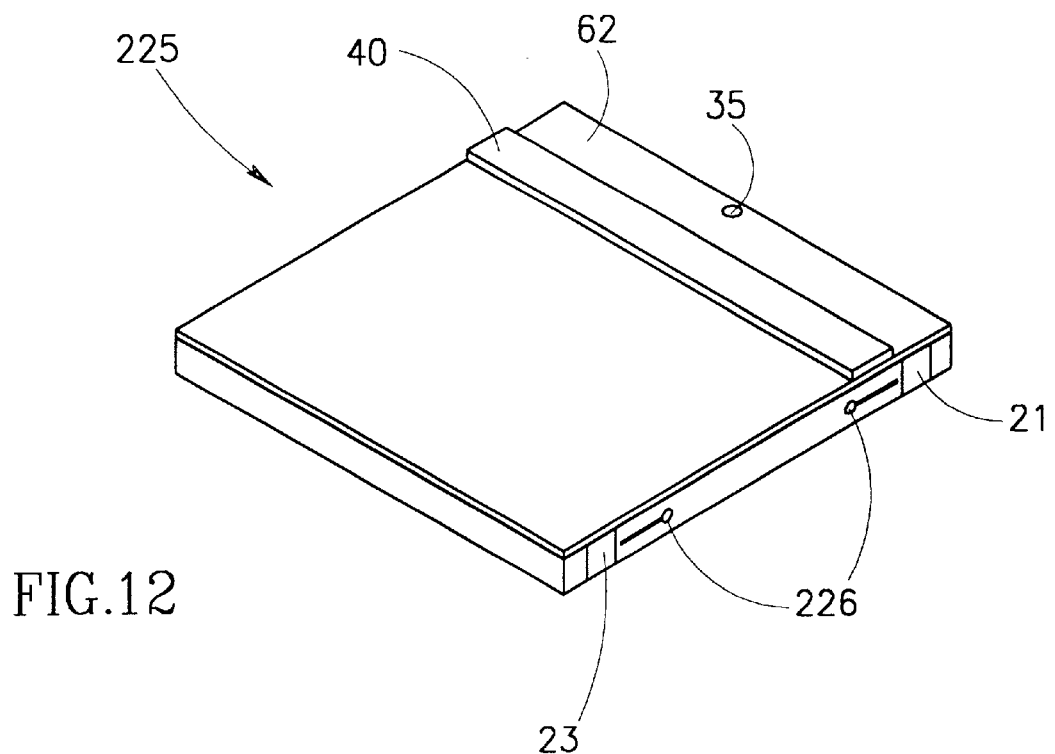
FIG. 12 is a schematic isometric illustration of an electrophoresis cassette, constructed and operative in accordance with a further preferred embodiment of the present invention.

Reference is now made to FIGS. 5 and 6 which illustrate an electrophoresis cassette, generally referenced 25, constructed and operative in accordance with a second preferred embodiment of the present invention.

Cassette 25 is generally similar in construction and operation to cassette 10 (FIGS. 1–4), i.e. it is a closed disposable cassette preferably used for a single electrophoresis test which comprises a gel 18 and an ion exchange matrices 20 and 22. Therefore similar elements of cassettes 10 and 25 are referenced by similar reference numerals (e.g. comb 40).

Chamber 60 comprises similar to chamber 11 a gel matrix 18 and an ion exchange matrices 20 and 22. However, chamber 60 differs from chamber 11 in construction and operation with respect to the anode and cathode and the gas accumulation and venting mechanism.

Chamber 60 comprises two conductive strips 21 and 23 which from the cathode and anode, respectively. Cathode 21 is diagonally supported by a diagonal ramp 27, ramp 27 preferably forms an integral part of chamber 60. Anode 23 is positioned under ion exchange matrix 20 and an additional gel matrix 29 which shrinks during electrophoresis due to electroendosmosis as described in detail hereinbelow. Gel matrix 29 is preferably the same gel as gel matrix 18, however its gel strength is lower than that of gel 18. For example, gel matrix 18 is comprised of 2% agarose while the gel matrix 29 comprises 0.3% agarose.

In operation, during an electrophoresis test, water flows from the anode side to the cathode side of the gel matrices due to electroendosmosis. Consequently, gel matrix 29 gradually shrinks, thereby creating a space in which gases generated in the vicinity of anode 23 accumulate.

According to a further preferred embodiment of the present invention, cathode 21 and anode 23 are made of a conductive material that is capable of adsorbing gases produced during the electrophoretic separation process.

In a preferred embodiment, cathode 21 and anode 23 are made of aluminum. During electrophoresis, the oxygen produced at the vicinity of anode 23 reacts with the aluminum anode to form aluminum oxide, whereby less free oxygen is produced at the anode side. The reduction in the volume of gas produced, together with the space created for gas accumulation by the shrinkage of gel matrix 29, alleviates the need for a vent hole in the anode side of cassette 25. Thus, cassette 25 may include in its cover 62 only a single vent hole 35 above empty volume 30 which is adjacent to the cathode.

In an alternative embodiment, the anode is made of aluminum as described hereinabove whereas the cathode is formed of palladium or any other suitable conductive material which adsorbs hydrogen at the cathode side.

Yet another particular feature of cassette 25 is that cathode 21 is diagonally supported by ramp 27. This facilitates continuous contact between the cathode and the surface of the anion exchange matrix 22 overlying cathode 21, whereby release of gas bubbles produced at the vicinity of cathode 21 are directed towards empty volume 30.

In a preferred embodiment, ramp 27 is formed as an integral part of chamber 60 and is inclined to the bottom wall 12 at an angle of about 45 degrees.

Reference is now made to FIGS. 7–11 which illustrate an electrophoresis cassette, generally referenced 125, constructed and operative in accordance with yet another preferred embodiment of the present invention. Cassette 125 similarly to cassettes 10 and 25 is a closed disposable cassette used for a single electrophoresis test and including all the chemical compounds required for driving the electrophoresis separation and for enabling visualization of its results when DNA as well as RNA or protein molecules have been separated.

Cassette 125 comprises a three dimensional chamber 160 generally similar to chamber 60 of cassette 25 and a cover 162 generally similar to cover 62 of cassette 25. Cassette 125 differs from cassette 25 in its ion source for driving the electrophoresis separation. In the illustrated embodiment, elements which are generally similar to elements of cassette 10 and 25 are designated by similar reference numerals (e.g. gel 18).

In chamber 160, the body of gel 18 is disposed intermediate two spaces 120 and 122 containing a buffer solution, such as the TAE buffer solution described hereinabove. Each of volumes 120 and 122 comprises therein a closed reservoir which includes the same buffer however in a higher concentration so as to provide the ions for driving the electrophoresis separation. In the illustrated preferred embodiment, the closed reservoirs are breakable ampoules 116 and 134 including buffer solutions 124 and 132, respectively which are of higher concentration than that of volumes 120 and 122. As a non limiting example, the concentration of solutions 124 and 132 is fifty fold higher than that of the buffer solutions of spaces 120 and 122.

It will be appreciated that ampoules 116 and 134 are formed of any sealed suitable material impermeable to water, such as plastic or glass, thus the concentrated buffer solutions 124 and 132 therein are not in contact with the buffer solutions filling volumes 120 and 122.

In the illustrated embodiment ampoules 116 and 134 are supported by ampoule supports 106. In operation, the user breaks ampoules 116 and 134 so as to provide the ions in the high concentration buffers 124 and 132, respectively, in order to provide the ions required to run the electrophoresis test, preferably, after the DC current is provided to cassette 126.

In the illustrated embodiment, each of ampoules 116 and 134 is supported under a flexible cover 110. Flexible covers 110 are formed of any flexible material responsive to mechanical force, such as rubber, so as to enable breaking of ampoules 116 and 134 once pressure is applied thereon, thereby releasing their contents into buffer spaces 120 and 122 respectively.

Optionally, concentrated buffer solution 124 also contains a suitable material for DNA staining, preferably any source for ethidium cations, such as ethidium bromide so as to enable UV visualization of the separated DNA samples as described hereinabove. In this case, chamber 160 is formed of a UV transparent material.

Reference is now made to FIGS. 12–15 which illustrate an electrophoresis cassette, generally reference 225, constructed and operative in accordance with yet another preferred embodiment of the present invention. Cassette 225 is similar to cassette 125 and similarly to cassettes 10 and 25 and 125 is a closed disposable cassette used for a single electrophoresis test and including all the chemical compounds required for driving the electrophoresis separation and for enabling visualization of its results when DNA as well as RNA or protein molecules have been separated.

Cassette 225 is generally similar to cassette 125 in construction and operation and similar elements are referenced by similar reference numerals. Cassette 225 differs from cassette 125 in its ampoule and its mechanism for breaking it.

Figure 13:
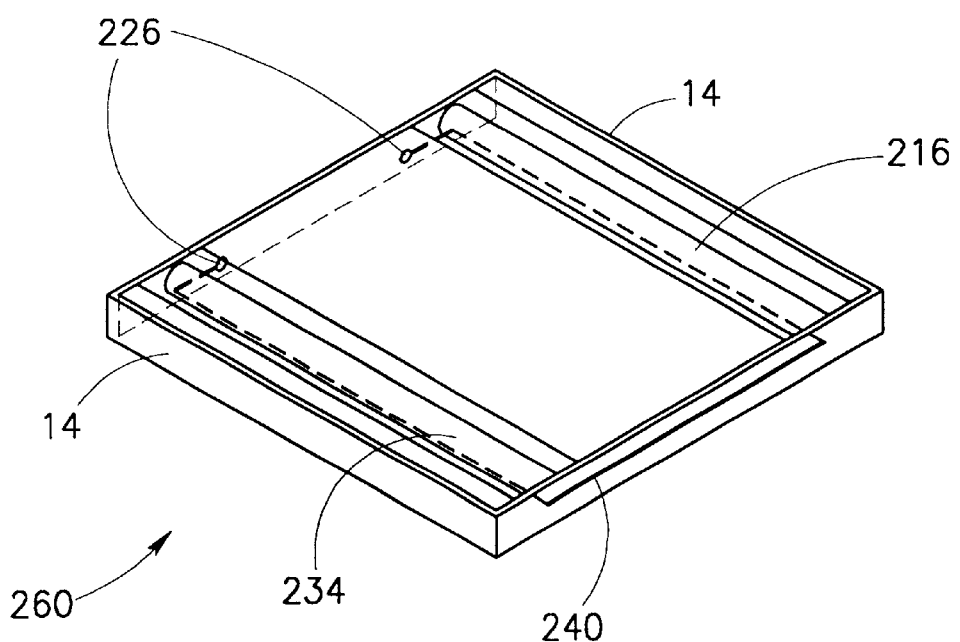
FIG. 13 is a bottom up cut away schematic isometric illustration of the electrophoresis cassette of FIG. 12.
Figure 14:
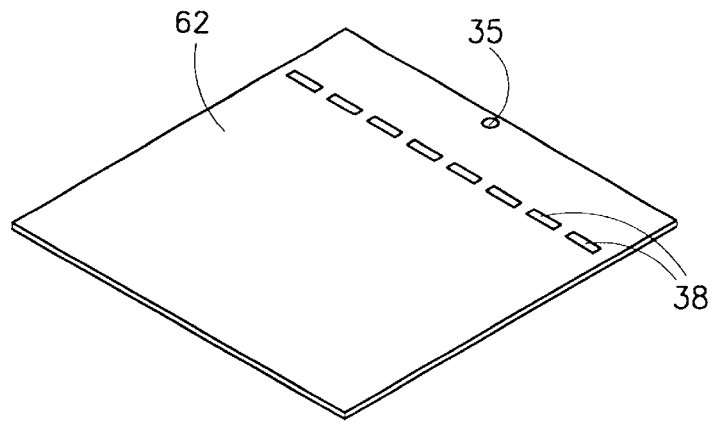
FIG. 14 is a schematic isometric exploded illustration of the electrophoresis cassette of FIG. 12.
Figure 15:
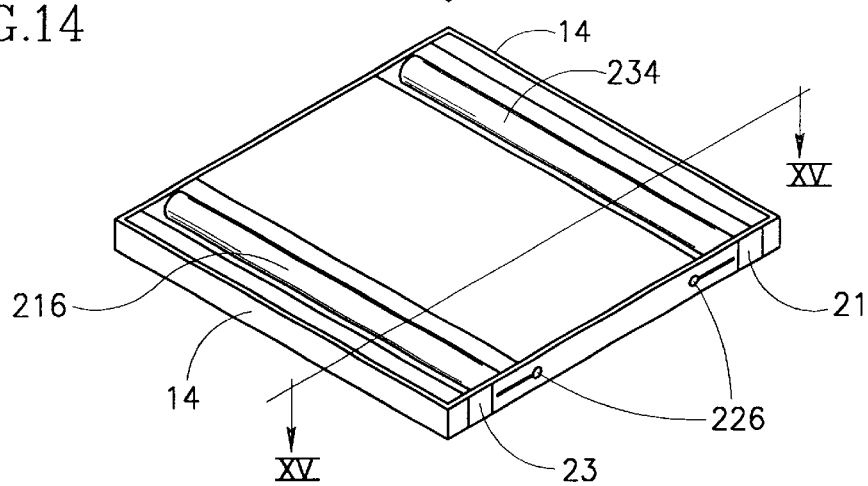
FIG. 15 is a schematic cross section illustration along lines XV—XV in FIG. 14.
Figure 15:
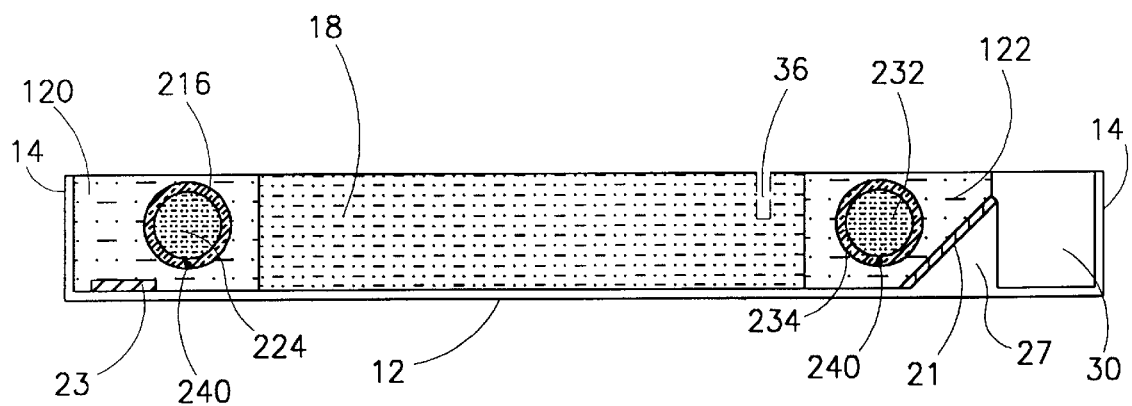

Cassette 225 comprises two ampoules 216 and 234 generally similar to ampoules 116 and 134 which are capable of melting by passing an electric current therethrough. As best seen in FIG. 13, a conducting wire 240 is embedded in the wall of ampoules 216 and 234. In the illustrated embodiment, conducting with 240 is a high resistivity single wire having two ends 226 to which electric current in a closed circuit may be applied.

In operation, ampoules 216 and 234 are melted just before he electrophoretic test is started by passing a current through conductive wire 240 by connecting an electrical power source to contacts 226. Preferably, the portions of conductive wire 240 not embedded in ampoules 216 and 243 are coated with an insulating material so as to insulate them.

Figure 16:
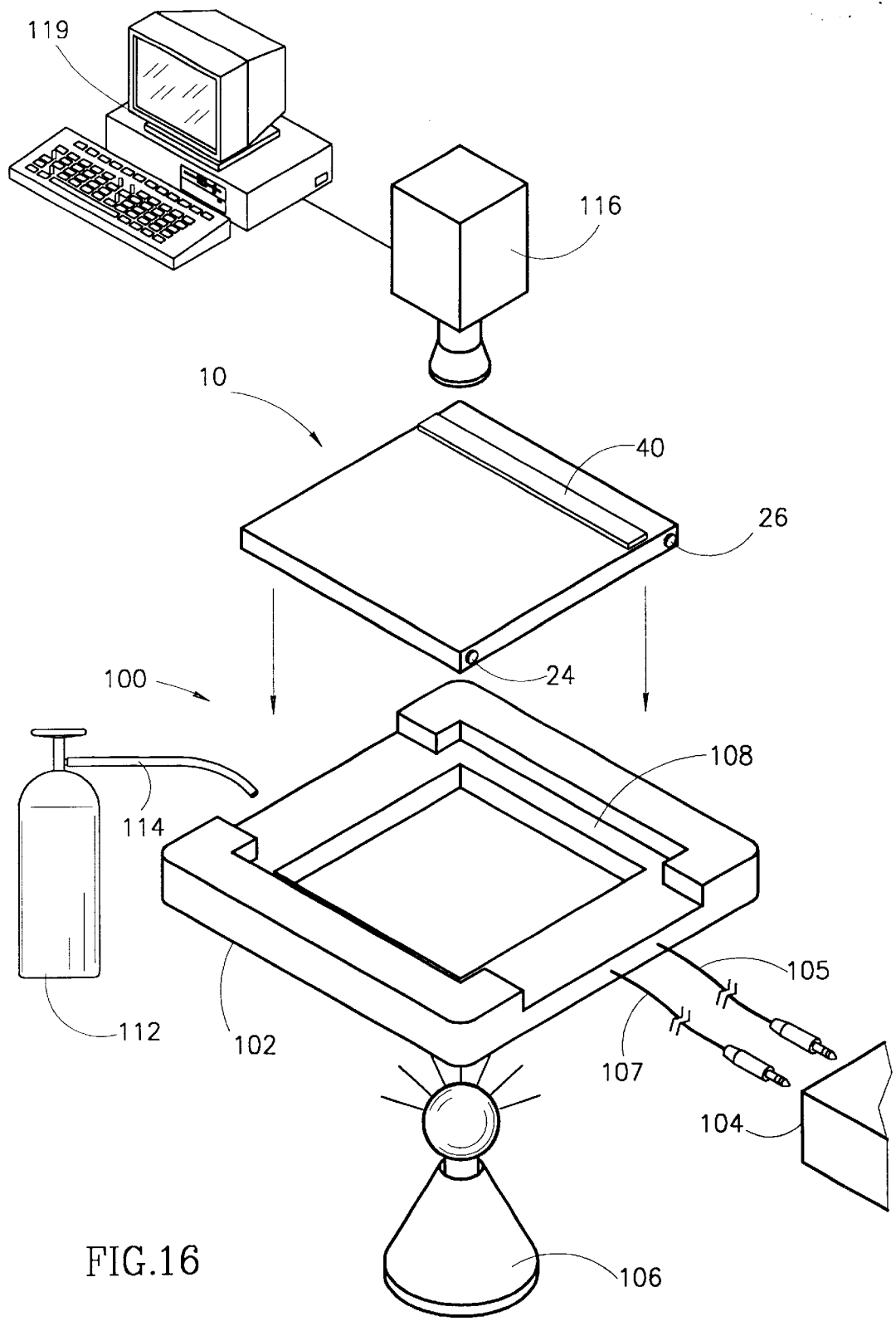
FIG. 16 is schematic isometric illustration of a system for electrophoresis, constructed and operative in accordance with another preferred embodiment of the present invention.

Reference is now made to FIG. 16 which is a schematic isometric illustration of a system for conducting a plurality of electrophoresis tests and which is suitable for visualizing and documenting, in situ, the results thereof, constructed and operative in accordance with a preferred embodiment of the present invention. The system, generally referenced 100, preferably comprises a holder or support housing 102 for supporting any of cassettes 10, 25, 125 or 225, a power supply 104 for providing the direct current (DC) required for driving the electrophoresis separation process, a cable 105 for connecting any of cassettes 10, 25, 125 and 225 to power supply 104 and an ultra violet (UV) light source 108 for illuminating the cassettes 10, 25, 125 or 225.

Holder 102 preferably comprises two contact points (not shown) to which the rods 24 and 26 of the cassette 10, or strips 21 and 23 of cassettes 25, 125 or 225 are connected so as to provide thereto the electric field required for the electrophoresis separation.

Optionally, system 100 also comprises a second cable 107 for providing the current required to heat conductive wire 240 in case cassette 225 is used. Accordingly, holder 102 includes an additional pair of contacts to which contacts 226 of cassette 225 are connected so as to provide thereto the electric current required for the heating conductive wire 240.

Another optional feature of system 100 is means for cooling any of cassettes 10, 25, 125, or 225, during the electrophoresis test, such as a flow of cooled gas, for example, liquid nitrogen, schematically illustrated by the balloon 112 and the tube 114.

In a preferred embodiment, system 100 also comprise means for documenting the electrophoresis separation results. In the illustrated embodiment these include a camera, preferably a video camera 116 and a computer 119 operatively connected to camera 116 and executing any suitable application for image analysis of the results of the electrophoresis separation.

It is a particular feature of system 100 that both the electrophoresis test, the visualization of the results thereof and optionally the documentation and the analysis thereof are performed when the cassette is in situ, i.e. in holder 102.

Unlike prior art electrophoresis systems for DNA molecules separation where the gel is taken and immersed in a UV sensitive marker, typically ethidium bromide, after the test, cassettes 10, 25, 125 and 225 preferably includes ethidium cations as described hereinabove so as to enable the visualization and thus the documentation and analysis of the electrophoresis test results.

In the embodiment illustrated in FIG. 16, the holder 102 is a stand alone open box-like construction which includes a support surface 108 on which any of cassettes 10, 25, 125 and 225 is placed. Alternatively, it may include a UV transparent bottom surface.

Another particular feature of the system 100 is that relative to prior art, a smaller number of operations is required from the user in order to conduct an electrophoresis test employing any of cassettes 10, 25, 125 and 225. These steps, for electrophoresis separation of DNA molecules, include:

A. A sample which includes the DNA molecules to be separated is introduced in wells;
B. For cassettes 125 and 225 only, ampoules 118 and 134 are broken;
C. The electrical current is switched on;
D. If it is desired to expedite the separation the cooled gas flow is also used;
E. As a result of steps A and C; A, B and C; A, C and D; or A, B, C and D; both electrophoresis separation and interaction of a UV detectable compound with the separated DNA molecules take place at the same time;
F. The UV lamp 106 is turned on to visualize the results of the separation. The results may be also recorded by the video camera 116;
G. The results may be transmitted on line to compute 119 for on the light quantitative analysis of the electrophoresis test results; and
H. The user disposes the cassette 10.

It will be appreciated that the preferred embodiments described hereinabove are described by way of example only and that numerous modifications thereto, all of which fall within the scope of the present invention, exist. For example, any of the cassettes of the present invention may include a combination of the ion exchange matrix disposed at one side of the gel 18 and the closed reservoir disposed at the other end thereof. Another example which is within the scope of the present invention is a two dimensional cassette in which the ion sources are disposed on all four sides of gel 18.

Figure 17:
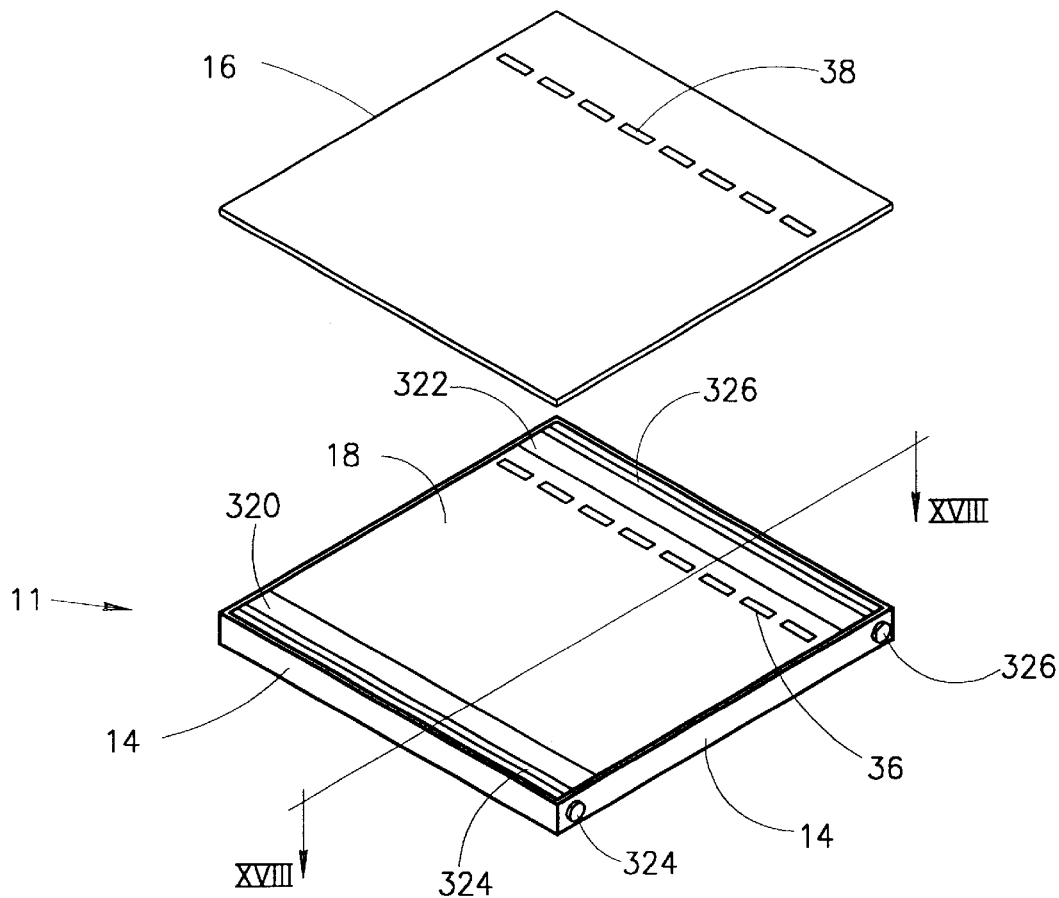
FIG. 17 is a schematic isometric exploded illustration of an electrophoresis cassette, constructed and operative in accordance with yet another preferred embodiment of the present invention.
Figure 18:
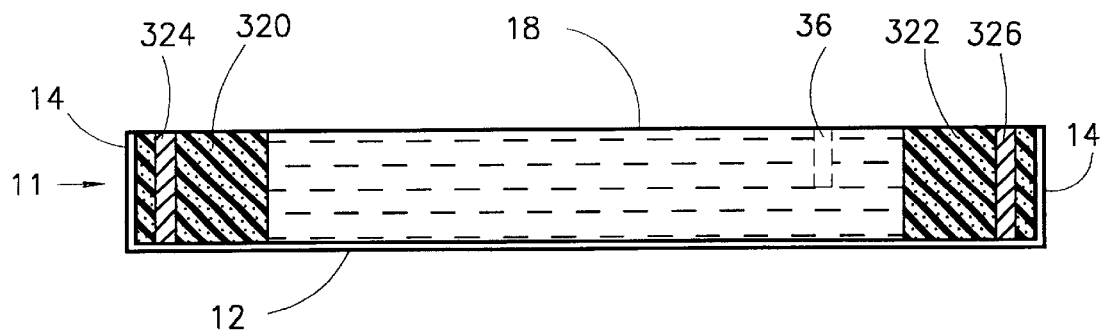
FIG. 18 is a schematic cross section illustration along lines XVIII—XVIII in FIG. 17.

Reference is now made to FIGS. 17 and 18 which illustrate a substantially closed disposable electrophoresis cassette, generally referenced 300, constructed and operative in accordance with yet another preferred embodiment of the present invention. Cassette 300 is generally similar to cassettes 10 and 25 in construction, and may be similarly used in apparatus 100 (FIG. 16). When protein molecules are being separated, the light source of apparatus 100 is either a visible or a U.V. light source. Similar elements in cassettes 10, 25 and 300 are referenced by similar reference numerals. It is noted that in the embodiment of FIGS. 17 and 18 the cover 16 does not include vent holes.

In the embodiment of FIGS. 17 and 18, cassette 300 comprises at the cathode end a metal rod 326 (the metal also referred to as M) and an ion source matrix 322, ion source matrix 322 is a suspension suspended in a a suitable gel matrix of a salt, such as a salt of the metal of the rod and providing ions for driving the electrophoresis separation. The salt is sparingly soluble in water and has the general formula $Y^{+n}{}_m(X^{-m})_n$, where n is the valency of the cation Y and $X^{-m}$ is an anion having a valency m.

In one preferred embodiment, Y is the metal cation and the salt has the general formula $M^{+n}{}_m(X^{-m})_n$, where n is the valency of the cation of metal M and $X^{-m}$ is an anion having a valency m. Alternatively, M and the cation of the salt are different.

The anode side includes another metal rod 324 and an the ion exchange matrix described in example 2 hereinabove. In one preferred embodiment, the cation exchange matrix 320 and the salt $Y^{+n}{}_m(X^{-m})_n$ of the ion source matrix 322 may be immersed in one of the materials used for preparing the gel.

In a preferred embodiment, the cation Y is selected to have suitable electrochemical properties such that when a suitable voltage difference is applied between the cathode 326 and the anode 324, some of the $Y^{+n}$ cations receive electrons from the cathode and becomes a neutral species.

Concomitantly, $X^{-m}$ anions move away from the cathode serving as charge carriers for the current flowing through cassette 300. Simultaneously, at the anode, atoms of the metal forming the anode loose electrons and pass into the cation exchange matrix 320 as $A^{+n}$ cations. In operation, $A^{+n}$ cations released at the anode displace cations which are bound to the cation exchange matrix 320. The $A^{+n}$ cations are thus substantially bound to the cation exchange matrix and prevented from migrating towards the cathode and possibly interfering with the molecules to be separated by binding thereto. The cations which are displaced from the cation exchange matrix 320 by the $A^{+n}$ cations, $Tris^{+1}$ cations in the illustrated nonlimiting example, move away from the anode, thus also serving as charge carriers for the current flowing through cassette 300.

In one preferred embodiment A, Y and M are similar. Alternatively one or more can differ form the others.

An advantage of cassette 300 is that the electrolysis of water at the anode and the cathode ends is substantially avoided, thus obviating the accumulation of gases at the cathode and the anode vicinity and the need for vent holes or gas absorbing means. Another advantage resulting from obviating electrolysis of water at the anode and the cathode ends is that there is substantially no production or buildup of hydroxyl and hydrogen ions at the cathode and the anode, respectively. Thus, the pH remains generally constant during the electrophoretic separation.

The following examples, which are not intended to limit the scope of the prevent invention, illustrate how the ion source matrix 322 and the metal rod 326 are prepared.

EXAMPLE 3

The ion source matrix 322 was prepared as follows:
A. A suspending gel of 3% agarose in 0.4X TAE buffer solution was prepared.
B. 0.6 grams of lead carbonate ($PbCO_3$), prepared by bubbling $CO_2$ into a solution of lead acetate following by filtration and wash by water of the precipitate, were suspended in 2 ml of the 3% agarose suspending gel of step A to obtain the ion source matrix 322.
C. A strip of lead metal was used as the cathode 326.

EXAMPLE 4

A. A suspending gel of 3% agarose in 0.4X TAE buffer solution was prepared.
B. 0.3 grams of silver chloride (AgCl) were suspended in 2 ml of the 3% agarose suspending gel of step A to obtain the ion source matrix 322.
C. A strip of aluminum metal was used as the cathode 326.

Figure 19:
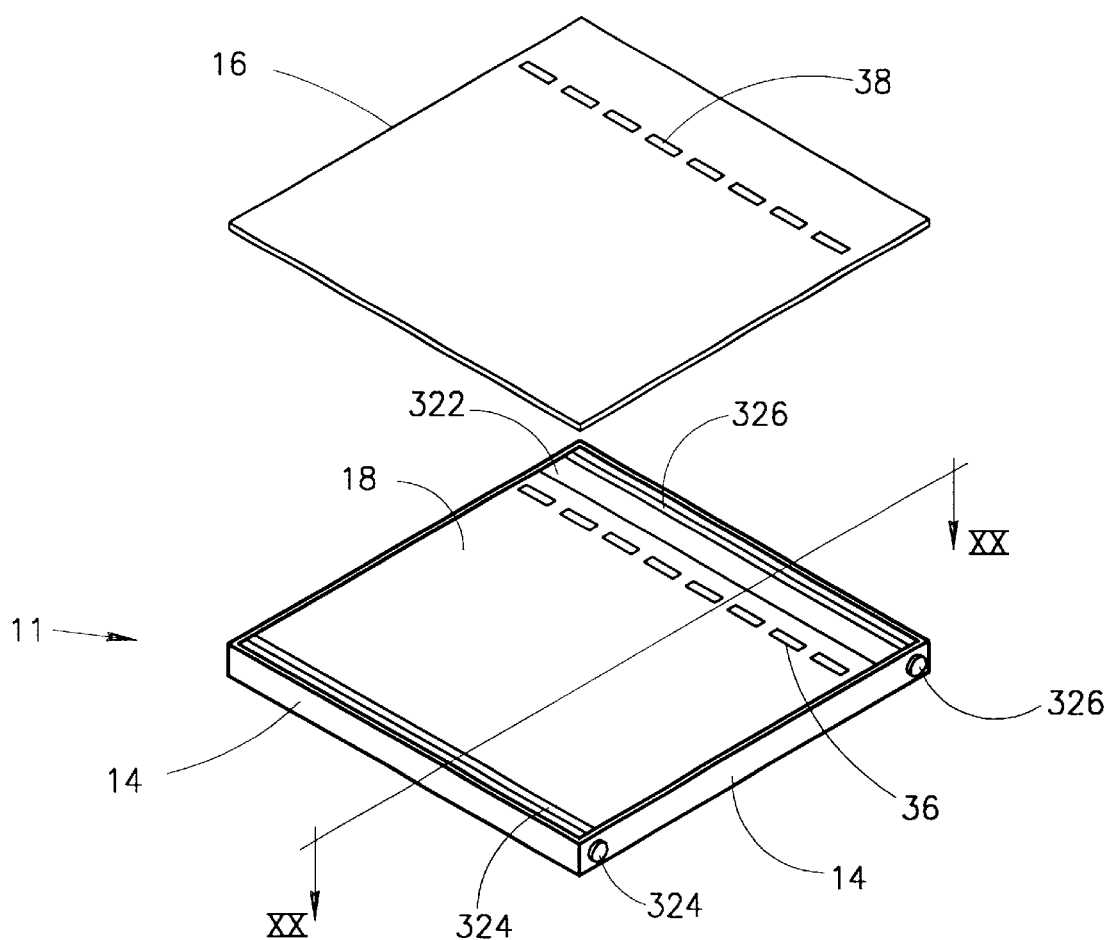
FIG. 19 is a schematic isometric exploded illustration of an electrophoresis cassette, constructed and operative in accordance with yet another preferred embodiment of the present invention.
Figure 20:
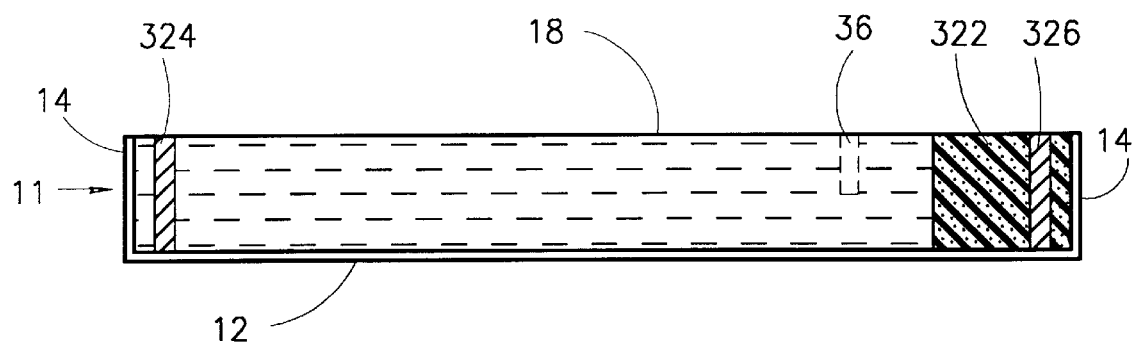
FIG. 20 is a schematic cross section illustration along lines XX—XX in FIG. 17.

Reference is now made to FIGS. 19 and 20 which illustrate a disposable electrophoresis cassette, generally referenced 400, constructed and operative in accordance with yet another preferred embodiment of the present invention. Cassette 400 is generally similar to cassette 300 in construction, in operation and may be similarly used in apparatus 100 (FIG. 16). It is noted that in the embodiment of FIGS. 19 and 20 the cover 16 does not include vent holes.

Cassette 400 having an anode and which is different from that of cassette 300. Specifically, while in cassette 300 the conductive metal rod 324 is embedded in the cation exchange matrix 320, the conductive metal rod 324 of cassette 400 is embedded in the body of separating gel 18 (FIG. 20).

During electrophoresis separation, at the anode and, metal atoms A loose electrons to the anode and pass into the separating gel matrix 18 as $A^{+n}$ cations, in the illustrated embodiment of FIGS. 19 and 20, the $A^{+n}$ cations released at the conductive rod 324, which is the anode, move away from the anode, thus, serving as charge carriers for the current flowing through the cassette 400. Thus, in contrast to the cassette 300 in which the $A^{+n}$ cations, which are electrochemically produced in the anode, bind to the cation exchange matrix 320 and release other cations which serve as the charge carriers, the $A^{+n}$ cations which are electrochemically produced at the anode of the cassette 400 move away from the anode, thus serving as charge carriers.

It will be appreciated that in cases where the metal cations $A^{+n}$ may interfere with the molecules to be separated by binding to the molecules or by chemically interacting with them, the metal cations can be prevented from reaching the separated molecules by increasing the length of the body of separating gel 18 between the rod 324 and the ion source matrix 322 so that during the electrophoresis separation, a sufficient degree of separation of the molecules will be achieved before any substantial amount of the metal cations $A^{+n}$ can reach the moving front of the separated molecules. Thus, the electrophoresis separation can be completed before the metal cations can substantially interfere with the separation.

It will further be appreciated that, similarly to cassette 300, there is substantially no electrolysis of water during the electrophoretic separation in the cassette 400.

It will still further be appreciated that the anode metal rod 324 in the cassettes 300 and 400 of FIGS. 17–20 and be made of different metals having suitable electrochemical properties wherein during electrophoresis run the electrochemical reaction wherein metal atoms of the metal rod loose electrons and enter solution as cations $A^{+n}$ occurs preferentially to electrolysis of water molecules. For example the metal rod can be made of lead, copper or silver.

In the preferred embodiment illustrated in FIGS. 17 and 18 the cation exchange matrix 320 which is in contact with the metal rod 324 can be any suitable cation exchange matrix such as the cation exchange matrix described in detail in examples 1 and 2 hereinabove, in these examples the cation exchange matrix 320 is also the source of ethidium cations for staining the separated DNA or RNA molecules.

In the preferred embodiment illustrated in FIGS. 19 and 20, the anode metal rod 324 is in contact with the separating gel 18. In this preferred embodiment, the separating gel 18 can contain the dye for staining the separated molecules. For example the separating gel 18 can be made of 2% agarose gel prepared in 0.4X TAE solution and containing 0.2 µg/ml of ethidium bromide. Thus, during the electrophoresis separation the ethidium bromide in the separating gel 18 can interact with the separated DNA or RNA molecules and enable their visualization.

Figure 21:
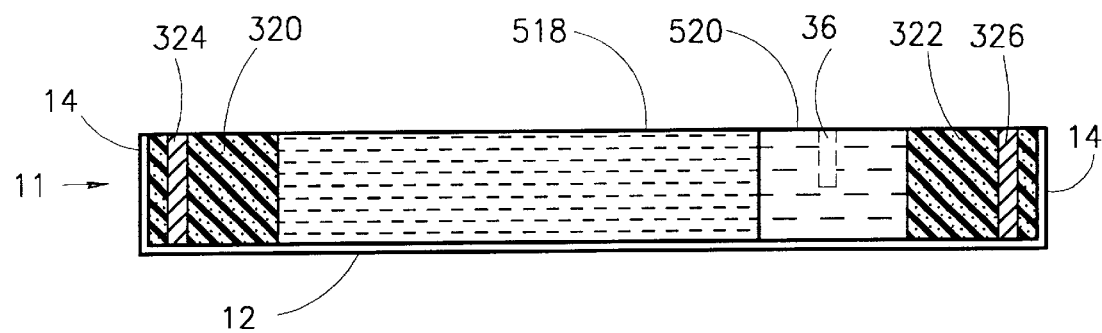
FIG. 21 is a schematic cross section illustration of a chamber of an electrophoresis cassette constructed and operative in accordance with yet another preferred embodiment of the present invention.
Figure 22:
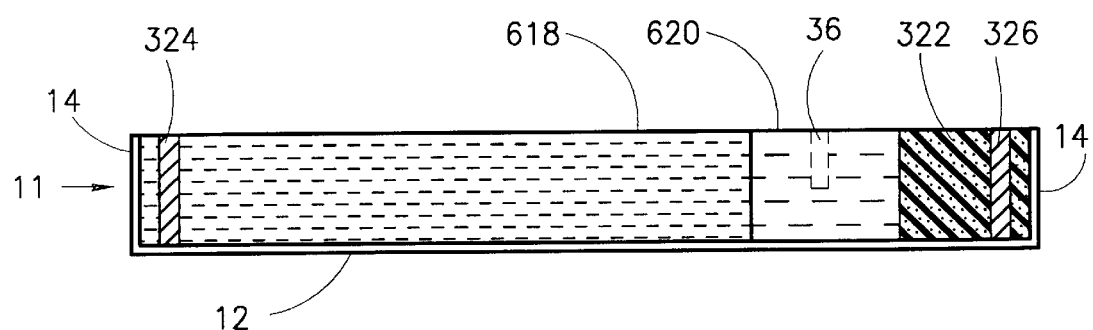
FIG. 22 is a schematic cross section illustration of a chamber of an electrophoresis cassette in accordance with still another preferred embodiment of the present invention.

Reference is now made to FIGS. 21 and 22 which illustrate two alternative chambers for the cassettes 300 and 400, respectively particularly suitable for electrophoresis separation of proteins.

In the chamber 11 of cassette 300, illustrated in FIG. 21, the body of separating gel 18 is replaced by a body of stacking gel 520 and a body of separating gel 518 which is in contact with the body of stacking gel 520. The wells 36 are positioned within the stacking gel 520.

In the chamber 11 of cassette 400, illustrated in FIG. 22, the body of separating gel 18 is replaced by a body of stacking gel 620 and a body of separating gel 618 which is in contact with the body of stacking gel 620. The wells 36 are positioned within the stacking gel 620.

The following examples, which are not intended to limit the scope of the present invention, illustrate how the separating gels 518 and 618 of FIGS. 21 and 22, respectively, and their corresponding stacking gels 520 and 620, respectively, are prepared.

EXAMPLE 5

The stacking gels 520 and 620 were prepared as follows:
A. The following ingredients were mixed together; 1 ml of 40% (w/v) acrylamide, 0.4 ml of 2% (w/v) bis-acrylamide, 0.4 ml of 0.5M Tri- HCl buffer having a pH of 6.8, 0.1 ml of 10% (w/v) SDS, 10 µl of N,N,N',N' tetramethylethylenediamine (TEMED) and 8 ml of deionized water.
B. 75 µl of a freshly prepared 10% (w/v) solution of ammonium persulphate were added to the mixture of step A and the resulting mixture was thoroughly mixed.

EXAMPLE 6

The separating gels 518 and 618 were prepared as follows:
A. The following ingredients were mixed together: 7.5 ml of 40% (w/v) acrylamide, 3.9 ml of 2% (w/v) bis-acrylamide, 7.5 ml of 1.5M Tris- HCl buffer having a pH of 8.8, 0.3 ml of 10% (w/v) SDS, 3.0 ml of a Tris-glycine buffer solution having a final concentration of 250 mM Tris and 1.92M glycine and a pH of 8.3, 30 µl of TEMED and 7.8 ml of deionized water.

B. 220 µl of a freshly prepared 10% (w/v) solution of ammonium persulphate were added to the mixture of step A and the resulting mixture was thoroughly mixed.

The following example, which is not intended to limit the scope of the present invention, illustrate how the cation exchange matrix 320 of FIG. 21, is prepared for use in the electrophoretic separation of proteins.

EXAMPLE 7

The cation exchange matrix 320 is prepared as follows:

A. 5 grams of swollen CM-25-120 Sephadex particles were placed in a standard column and washed with 200 ml of 0.625 Molar glycine solution, having a pH of 7.0 as adjusted with Trizma base solution.

B. The CM-25-120 Sephadex particles were washed with 7 volumes of distilled water.

C. The CM-25-120 Sephadex particles were kept in two volumes of a tris-glycine buffer of the following composition: 0.192M glycine, 25 mM Tris having a pH of 8.3 as adjusted with Trizma base solution.

D. 1.5 ml of the CM-25-120 Sephadex particles were suspended in 1 ml of 3% agarose in tris-glycine buffer to form the cation exchange matrix 320 of cassette 300.

In a nonlimiting embodiment, the support matrix in which the sparingly soluble metal salt is suspended, can be made of agarose gel as described in examples 3 and 4 hereinabove, while the stacking gels 520 and 620 and the separating gels 518 and 618 can be made of acrylamide gel as described in examples 5 and 6 hereinabove.

In a preferred embodiment, when proteins are undergoing electrophoretic separation in cassettes 300 and 400, the separated protein molecules are visualized in situ by including a suitable ion protein dye source in the cassette. A nonlimiting example for an ionic protein dye is the anionic protein dye ChromaPhor Stain, commercially available from Promega Corporation of Madison, U.S.A. During electrophoresis, some of the negatively charged dye ions stain the separated protein molecules in situ so that the progress of the separation process can be visualized using system 100 (FIG. 16) with a visible light source instead of the UV light source 106.

It will be appreciated that the present invention is not limited by what has been described hereinabove and that numerous modifications, all of which fall within the scope of the present invention, exist. For example, while the present invention has been described with reference to a substantially closed cassettes, the ion source a described hereinabove can be used for any other electrophoresis apparatus, such as an open cassette.

Another example is to use only one of the cathode and anode for providing ions for driving the electrophoresis separation, in one example, the cathode is made of a strip of aluminum in contact with an anion exchange matrix and the anode is made of a strip of lead being in contact with a cation exchange matrix. In another example, the cathode is made of a strip of lead in contact with an ion source matrix which contains a support gel matrix in which lead carbonate is suspended and the anode is made of a strip of copper in contact with a cation exchange matrix.

It will be appreciated by persons skilled in the art that the present invention is not limited to what has been particularly shown and described hereinabove. Rather, the scope of the present invention is defined only by the claims that follow:

What is claimed is:

1. An apparatus for conducting electrophoresis, the apparatus comprising:
   a chamber with walls defining an electrophoresis area, said electrophoresis area comprising at least one gel matrix for facilitating said electrophoresis;
   electrodes within said chamber and in contact with said gel matrix, wherein said electrodes are an anode and a cathode; and
   a cation exchange matrix in contact with said anode and with said gel matrix, wherein ions released from said anode are exchangeable with ions released from said body of cation exchange matrix.

2. The apparatus of claim 1 wherein said anode is copper.

3. The apparatus of claim 1 wherein said walls comprise side walls, a bottom wall and a cover so as to enable said chamber to be substantially closed before, during and after said electrophoresis.

4. An apparatus for conducting electrophoresis, the apparatus comprising:
   a chamber with walls defining an electrophoresis area, said electrophoresis area comprising at least one gel matrix for facilitating said electrophoresis;
   electrodes within said chamber and in contact with said gel matrix, wherein said electrodes are an anode and a cathode; and
   a dye source within said gel matrix, said dye source providing a dye for enabling visualization of said electrophoresis.

5. The apparatus of claim 5 wherein said walls comprise side walls, a bottom wall and a cover so as to enable said chamber to be substantially closed before, during and after said electrophoresis.

6. An apparatus for conducting electrophoresis comprising:
   a chamber with walls defining an electrophoresis area, said electrophoresis area comprising at least one gel matrix for facilitating said electrophoresis;
   electrodes within said chamber and in contact with said gel matrix, wherein said electrodes are an anode and a cathode; and
   a matrix in contact with said cathode comprising at least one salt, wherein said salt is sparingly soluble in water; said gel matrix comprising ions, said ions generated during an electrochemical reaction of said matrix in contact with said cathode.

7. The apparatus of claim 6 wherein said walls comprise side walls, a bottom wall and a cover so as to enable said chamber to be substantially closed before, during and after said electrophoresis.

8. The apparatus of claim 6, wherein said gel matrix is substantially free from hydrogen gas during said electrophoresis.

9. The apparatus of claim 6, wherein said anode is copper.

10. The apparatus of claim 6 wherein said salt is in contact with an anion exchange matrix for replacing anions of said salt with anions of said anion exchange matrix.

11. The apparatus of claim 6, wherein said gel is an aqueous gel and wherein said electrochemical reaction does not include water electrolysis.

12. The apparatus of claim 6 wherein said chamber further comprises a dye source within said gel matrix, said dye source providing a dye for enabling visualization of said electrophoresis.

13. The apparatus of claim 6 wherein said anode is selected from the group consisting of lead, silver and copper.

14. The apparatus of claim 6 wherein said electrodes are the anode and the cathode disposed at a first and second end of said gel matrix, respectively.

15. An apparatus for conducting electrophoresis comprising:
a chamber with walls defining an electrophoresis area, said electrophoresis area comprising at least one gel matrix for facilitating said electrophoresis;
electrodes in contact within said chamber and in contact with said gel matrix, wherein said electrodes are an anode and a cathode; and
a matrix in contact with said cathode comprising at least one sparingly water-soluble salt;
said gel matrix comprising ions, said ions generated during electrochemical reactions of said anode and of said matrix in contact with said cathode.

16. The apparatus of claim 18 wherein said walls comprise side walls, a bottom wall and a cover so as to enable said chamber to be substantially closed before, during and after said electrophoresis.

17. The apparatus of claim 15 wherein said anode comprises metal.

18. The apparatus of claim 15 wherein said gel is an aqueous gel and wherein said electrochemical reactions does not include water electrolysis.

19. The apparatus of claim 15, wherein said gel matrix is substantially free from hydrogen and oxygen gas during said electrophoresis.

20. The apparatus of claim 15, wherein said anode is copper.

21. The apparatus of claim 15 wherein said chamber further comprises of dye source within said gel matrix, said dye source providing a dye for enabling visualization of said electrophoresis.

22. The apparatus of claim 15, wherein said anode is selected from the group consisting of lead, silver and copper.

23. The apparatus of claim 15, wherein said electrodes are the anode and the cathode disposed at a first and second end of said body of separating gel, respectively.

24. The apparatus of claim 15, wherein said cathode comprises metal.

25. The apparatus of claim 24 wherein said metal is selected from the group consisting of aluminum, copper, lead and silver.

26. The apparatus of claim 18 wherein said chamber further comprises a body of stacking gel, said body of stacking gel being in contact with said body of separating gel.

27. The apparatus of claim 15, additionally comprising a cation exchange matrix, said cathode is in contact with said salt and said anode is in contact with said cation exchange matrix.

28. The apparatus of claim 27 wherein said salt is in contact with an anion exchange matrix for replacing anions of said salt with anions of said anion exchange matrix.

29. The apparatus of claim 15 wherein said salt is in contact with an anion exchange matrix for replacing anions of said salt with anions of said anion exchange matrix.

30. A method for electrophoresis separation, the method comprising the steps of:
introducing a test sample into a gel;
applying an electrical field to said gel; and
driving an electrophoresis separation by releasing ions required for maintaining an electrical field by degradation of a metal anode.

31. The method of claim 29, wherein said step of driving an electrophoresis separation does not include water electrolysis.

32. A method for electrophoresis separation, the method comprising the steps of:
introducing a test sample into a gel;
applying an electrical field to said gel; and
driving an electrophoresis separation by releasing ions required for maintaining an electrical field by degradation of a sparingly water-soluble salt in contact with a cathode.

33. The method of claim 32, wherein said step of driving an electrophoresis separation does not include water electrolysis.

34. A method for electrophoresis separation, the method comprising the steps of:
introducing a test sample into a gel;
applying an electrical field to said gel; and
driving an electrophoresis separation by releasing ions required for maintaining an electrical field by degradation of a metal anode and degradation of a sparingly water-soluble salt in contact with a cathode.

35. The method of claim 33, wherein said step of driving an electrophoresis separation does not include water electrolysis.

* * * * *

UNITED STATES PATENT AND TRADEMARK OFFICE
CERTIFICATE OF CORRECTION

PATENT NO. : 6,379,516 B1
DATED : April 30, 2002
INVENTOR(S) : Cabilly, Shmuel et al.

It is certified that error appears in the above-identified patent and that said Letters Patent is hereby corrected as shown below:

Column 18,
Line 31, please delete the term "claim 5" and insert in lieu of -- claim 4 --

Column 19,
Line 17, please delete the term "claim 18" and insert in lieu of -- claim 15 --
Line 44, please delete the term "claim 18" and insert in lieu of -- claim 15 --

Column 20,
Line 19, please delete the term "claim 29" and insert in lieu of -- claim 30 --
Line 43, please delete the term "claim 33" and insert in lieu of -- claim 34 --

Signed and Sealed this

Fifth Day of November, 2002

*Attest:*

JAMES E. ROGAN
*Attesting Officer*   *Director of the United States Patent and Trademark Office*